United States Patent [19]
Lai et al.

[11] Patent Number: 5,486,579
[45] Date of Patent: * Jan. 23, 1996

[54] WETTABLE SILICONE HYDROGEL COMPOSITIONS AND METHODS FOR THEIR MANUFACTURE

[75] Inventors: Yu-Chin Lai; Paul L. Valint, Jr., both of Pittsford, N.Y.

[73] Assignee: Bausch & Lomb Incorporated, Rochester, N.Y.

[*] Notice: The portion of the term of this patent subsequent to May 10, 2011, has been disclaimed.

[21] Appl. No.: 226,596

[22] Filed: Apr. 11, 1994

Related U.S. Application Data

[63] Continuation of Ser. No. 922,292, Jul. 30, 1992, abandoned, which is a continuation-in-part of Ser. No. 788,013, Nov. 5, 1991, abandoned.

[51] Int. Cl.$^6$ .................................................. C08F 283/12
[52] U.S. Cl. .................... 525/479; 528/26; 528/32; 528/41; 528/25; 351/160 R; 351/160 H; 526/279
[58] Field of Search ............... 525/479; 526/279; 351/160 R, 160 H; 528/32, 26, 41, 25

[56] References Cited

U.S. PATENT DOCUMENTS

| | | | |
|---|---|---|---|
| 3,408,429 | 10/1968 | Wichterle | 254/1 |
| 3,496,254 | 2/1970 | Wichterle | 264/1 |
| 4,084,459 | 4/1978 | Clark | 82/1 |
| 4,136,250 | 1/1979 | Mueller et al. | 528/29 |
| 4,153,641 | 5/1979 | Deichert et al. | 260/827 |
| 4,197,266 | 4/1980 | Clark et al. | 264/1 |
| 4,277,595 | 7/1981 | Deichert et al. | 528/26 |
| 4,343,927 | 8/1982 | Chang | 526/262 |
| 4,740,533 | 4/1988 | Su et al. | 523/106 |
| 4,810,764 | 3/1989 | Friends et al. | 526/245 |
| 4,910,277 | 3/1990 | Bambury et al. | 526/260 |
| 5,034,461 | 7/1991 | Lai et al. | 525/100 |
| 5,070,215 | 12/1991 | Bambury et al. | 556/418 |
| 5,310,779 | 5/1994 | Lai | 524/588 |
| 5,358,995 | 10/1994 | Lai et al. | 524/547 |

FOREIGN PATENT DOCUMENTS 0080539  8/1983  European Pat. Off. ............. 230/8

*Primary Examiner*—Melvyn I. Marquis
*Assistant Examiner*—Margaret W. Glass
*Attorney, Agent, or Firm*—Edward W. Black; Craig E. Larson

[57] ABSTRACT

Improved silicone-containing hydrogels are disclosed with enhanced wettability comprising a silicone-containing monomer, at least one acrylic-containing hydrophilic monomer, and at least one vinyl-containing hydrophilic monomer.

16 Claims, 1 Drawing Sheet

WETTABLE SILICONE HYDROGEL COMPOSITIONS AND METHODS FOR THEIR MANUFACTURE

This application is a continuation of U.S. Ser. No. 07/922,292 filed Jul. 30, 1992, now abandoned which is a continuation-in-part of U.S. Ser. No. 07/788,013 filed Nov. 5, 1991 and now abandoned.

BACKGROUND OF THE INVENTION

1. Field of the Invention

The present invention relates to improved wettable polymeric hydrogel compositions useful for the production of biomedical devices, especially contact lenses.

2. Background

Hydrogels have been a desirable class of material for the preparation of biomedical devices, and have been known since at least Wichterle, et al U.S. Pat. No. 3,220,960 which disclosed hydrogels comprising a hydrated polymer of a hydroxyalkyl acrylate or methacrylate crosslinked with a corresponding diester (poly 2-hydroxyethyl methacrylate, known as poly-HEMA).

A hydrogel is a hydrated crosslinked polymeric system that contains water in an equilibrium state. The physical properties of hydrogels can vary widely and are mostly determined by their water content. Since hydrogels exhibit excellent biocompatibility, there has been extensive interest in the use of hydrogels for biomedical devices, especially contact lenses.

In the field of contact lenses, various factors must combine to yield a material that has appropriate characteristics. Oxygen permeability, wettability, material strength and stability are but a few of the factors which must be carefully balanced to achieve a useable end-result contact lens. Since the cornea receives its oxygen supply exclusively from contact with the atmosphere, good oxygen permeability is a critical characteristic for any contact lens material.

It was discovered that certain crosslinked polymeric materials could be hydrated and retain their water content. It was further found that the higher the water content within contact lenses made from these crosslinked hydrogel polymers, the greater was the oxygen permeability through the lens to the cornea.

High water-containing hydrogels have at times exhibited undesirable mechanical properties. For example, such hydrogels are often not easily formed into hydrolytically stable lenses. Further such materials have at times exhibited tearing or other breakage as a result of poor tensile strength. What was needed was a highly oxygen permeable material that was durable and highly wettable. Wettability is important in that, if the lens is not sufficiently wettable, it does not remain lubricated and therefore cannot be worn comfortably in the eye. The optimum contact lens would have not only excellent oxygen permeability, but also excellent tear fluid wettability.

Silicone-containing materials were tried as viable contact lens materials and displayed very good oxygen permeability and durability. However, most silicone-containing materials are largely hydrophobic and therefore not sufficiently wettable. Further, it is believed that such hydrophobicity causes enhanced deposit problems, which may also result in discomfort when wearing contact lenses made from certain silicone-containing polymers.

Therefore, an optimal hydrogel material for biomedical devices, such as contact lenses, would have ideal rigidity, high oxygen permeability and a high degree of wettability.

SUMMARY OF THE INVENTION

In accordance with this invention, the surface wettability of hydrogels, such as silicone-containing hydrogels, and more specifically polyurethane-silicone hydrogels and ethylenically terminated polysiloxane hydrogels such as (poly)organosiloxane hydrogels, are significantly enhanced by incorporating both at least one vinyl-containing hydrophilic monomer and at least one acrylic-containing hydrophilic monomer into the monomer mix along with the silicone-containing monomer or prepolymer.

Further, in accordance with the present invention, a method for making a wettable silicone-containing hydrogel composition is disclosed comprising the steps of a) combining at least one vinyl-containing monomer, at least one acrylic-containing monomer and at least one silicone-containing monomer or prepolymer into a monomer mix and b) curing the monomer mix resulting from step a) to form a silicone-containing hydrogel composition.

It is believed that the combined vinyl-containing and acrylic-containing monomers act as wetting agents, and interact with the predominantly hydrophobic silicone-containing monomers and prepolymers in the monomer mix to produce highly wettable hydrogels with ideal rigidity. Such resultant hydrogels are especially well-suited for use as contact lens materials.

DETAILED DESCRIPTION OF THE INVENTION

Figure 1:
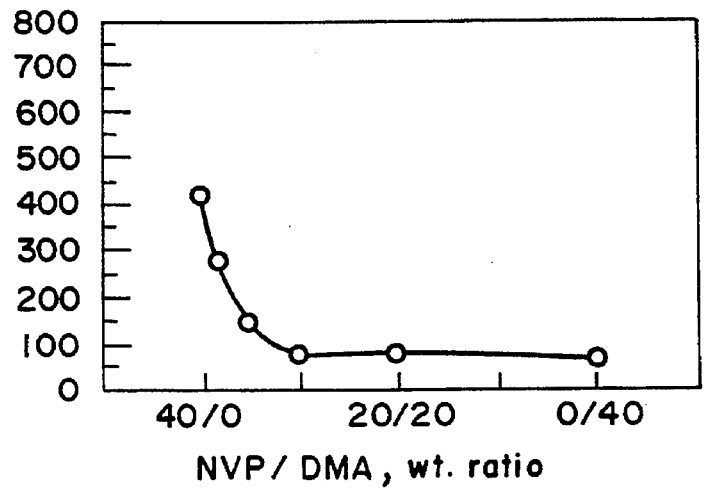
FIGS. 1 and 2 depict the effect on modulus of polyurethane films as the composition ratio of NVP to DMA is changed.

The present invention relates to improved wettability of hydrogels, especially silicone-containing hydrogels with ideal rigidity suitable for biomedical applications such as contact lenses.

The silicone-containing hydrogels of the present invention display improved wettability as a result of the combined presence in the monomer mix of at least one acrylic-containing monomer and at least one vinyl-containing monomer.

Silicone hydrogels (i.e., hydrogels containing silicone) are usually prepared by polymerizing a mixture containing at least one silicone-containing monomer and at least one hydrophilic monomer. Either the silicone-containing monomer or the hydrophilic monomer may function as a crosslinking agent (a crosslinker being defined as a monomer having multiple polymerizable fuctionalities) or a separate crosslinker may be employed.

The term "vinyl-containing" is meant to refer to non-acrylic monomers having the vinyl grouping ($CH_2$=CH—) which are generally highly reactive. Such vinyl groups are known to polymerize relatively easily. "Acrylic-containing" monomers are those compounds containing the acrylic grouping ($CH_2$=CRCOX) which are also generally reactive.

The vinyl-containing monomers used in the present invention include hydrophilic monomers such as N-vinyl pyrrolidone, N-vinyl-N-methyl acetamide, N-vinyl-N-ethyl acetamide, N-vinyl-N-methyl formamide, N-vinyl formamide, with N-vinyl pyrrolidone (NVP) being the most preferred.

The acrylic-containing monomers used in the present invention include hydrophilic monomers such as 2-hydroxyethyl methacrylate, glycerol methacrylate, 2-hydroxyethyl methacrylamide, N,N-dimethyl (meth)acrylamide, diacetone acrylamide, methacrylic acid and acrylic acid with N,N-dimethylacrylamide (DMA) being the most preferred.

When both vinyl- and acrylic-containing monomers are present within one monomer mixture, it is preferable to add a crosslinking composition containing at least one vinyl-containing polymerizable group and at least one acrylic- or styrene-containing polymerizable group disclosed in copending and commonly assigned U.S. application Ser. No. 07/788,071 filed Nov. 5, 1991 now U.S. Pat. No. 5,310,779 and having the following general schematic representation (I):

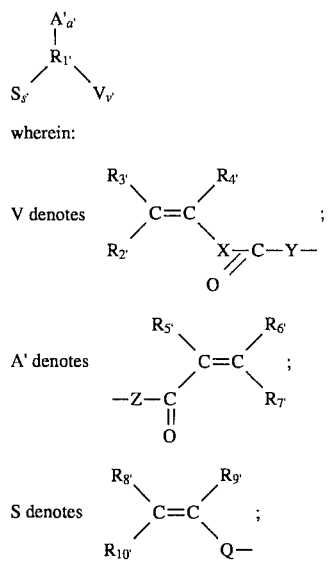

wherein:

$R_1$, is an alkyl radical derived from substituted and unsubstituted hydrocarbons, polyalkylene oxide, poly(perfluoro) alkylene oxide, dialkyl-capped polydimethylsiloxane, dialkyl-capped polydimethylsiloxane modified with fluoroalkyl or fluoroether groups;

$R_2'$-$R_{10'}$ are independently H, or alkyl of 1 to 5 carbon atoms;

Q is an organic group containing aromatic moieties having 6 to 30 carbon atoms;

X, Y, and Z are independently O, NH or S;

V' is 1, or higher; and a', s' independently are greater than or equal to 0, and a'+s'≧1.

The addition of crosslinking agents of Formula I assists in the copolymerization of the vinyl-and acrylic-containing monomers with each other as well as with other monomers and prepolymers present in the monomer mix, such as the relatively non-polar ring-containing oxazolone compounds of the general formula (II):

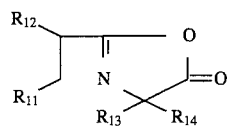

where $R_{11}$ and $R_{12}$ independently denote H or $CH_3$; and $R_{13}$ and $R_{14}$ independently denote methyl or cyclohexyl radicals.

These ring-containing monomers which may be incorporated into the silicone-containing hydrogels of the present invention specifically include 2-isopropenyl-4,4-dimethyl-2-oxazolin-5-one (IPDMO), 2-vinyl-4,4-dimethyl-2-oxazolin-5-one (VDMO), cyclohexane spiro-4'-(2'isopropenyl-2'-oxazol-5'-one) (IPCO), cyclohexane-spiro-4'-(2'-vinyl-2'oxazol-5'-one) (VCO), and 2-(-1-propenyl)-4,4-dimethyloxazol-5-one (PDMO). The preferred oxazolones are prepared by known reaction sequences set forth in commonly assigned U.S. Pat. No. 4,810,764. The amount of crosslinker used is about 0.01 to about 5% of the vinyl-containing monomer weight present in a useful formulation.

We have observed that silicone-containing hydrogels containing NVP as a wetting agent have a much higher modulus as compared with silicone hydrogels that incorporate acrylic-containing monomers, such as glycerol methacrylate and, N,N-dimethylacrylamide (DMA). We observed, and this invention contemplates, that the incorporation of a vinyl-containing hydrophilic monomer with an acrylic-containing hydrophilic monomer as wetting agents into silicone-containing formulations results in hydrogels suitable for biomedical applications, especially contact lenses.

Any known silicone-containing prepolymer may be used to form the silicone hydrogels of this invention, as will be apparent to one skilled in the art. The monomers added to the monomeric mixture may be monomers or prepolymers. A "prepolymer" is a reaction intermediate polymer of medium molecular weight having polymerizable groups. Thus it is understood that the terms "silicone-containing monomers" and "hydrophilic monomers" include prepolymers. Examples of such monomers may be found in U.S. Pat. Nos. 4,136,250; 4,153,641; 4,740,533; 5,034,461; and 5,070,215.

Further, notations such as "(meth)acrylate or " (meth)acrylamide are used herein to denote optional methyl sunstitution. Thus, for example, methyl (meth)acrylate includes both methyl acrylate and methyl methacrylate and N-alkyl (meth)acrylamide includes both N-alkyl acrylamide and N-alkyl methacrylamide.

One preferred class of suitable silicone-containing monomers are bulky polysiloxanylalkyl (meth)acrylic monomers represented by the formula (III):

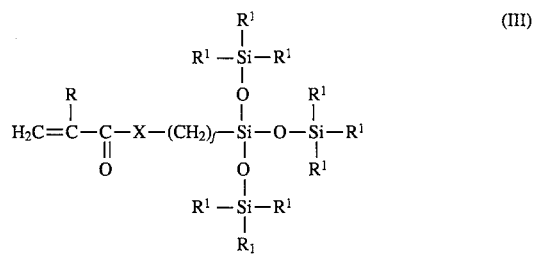

wherein:

X is O or NR;

each R is independently hydrogen or methyl; and each $R^1$ is independently a lower alkyl or phenyl group; and f is 1 or 3 to 10.

Such bulky monomers include methacryloxypropyl tris(trimethylsiloxy)silane, pentamethyldisiloxanylmethylmethacrylate, tris(trimethylsiloxy)methacryloxy propylsilane, phenyltetramethyldisiloxanylethyl acrylate, and methyldi(trimethylsiloxy)methacryloxymethyl silane.

A further preferred class of silicone-containing monomers are the poly(organosiloxane) prepolymers represented by the formula (IV):

$$A-(R^7)-\underset{\underset{R^4}{|}}{\overset{\overset{R^3}{|}}{Si}}-[O-\underset{\underset{R^6}{|}}{\overset{\overset{R^5}{|}}{Si}}]_n-O-\underset{\underset{R^4}{|}}{\overset{\overset{R^3}{|}}{Si}}-(R^7)-A \quad \text{(IV)}$$

wherein:

A is an activated unsaturated group, such as an ester or amide of an acrylic or a methacrylic acid;

each $R^3$–$R^6$ is independently selected from the group consisting of a monovalent hydrocarbon radical or a halogen substituted monovalent hydrocarbon radical having 1 to 18 carbon atoms which may have ether linkages between carbon atoms;

$R^7$ is a divalent hydrocarbon radical having from 1 to 22 carbon atoms; and n is 0 or an integer greater than or equal to 1.

A further preferred class of silicone-containing monomers are the monomers having the following schematic representations:

(V) E(*D*A"*D*G)$_a$*D*A"*D*E'; or (VI) E(*D*G*D*A")$_a$*D*G*D*E';

where

D denotes an alkyl diradical, an alkyl cycloalkyl diradical, a cycloalkyl diradical, an aryl diradical or an alkylaryl diradical having 6 to 30 carbon atoms;

G denotes an alkyl diradical, a cycloalkyl diradical, an alkyl cycloalkyl diradical, an aryl diradical or an alkylaryl diradical having 1 to 40 carbon atoms and which may contain ether, thio or amine linkages in the main chain;

* denotes a urethane or ureido linkage;

a is at least 1;

A" denotes a divalent polymeric radical of formula (VII):

$$-(CH_2)_m-\left[\underset{\underset{R^{s'}}{|}}{\overset{\overset{R^{s}}{|}}{Si}}-O\right]_p-\underset{\underset{R^{s'}}{|}}{\overset{\overset{R^{s}}{|}}{Si}}-(CH_2)_m-$$

wherein: $R^s$ and $R^{s'}$ independently denote an alkyl or fluoro-substituted alkyl group having 1 to 10 carbon atoms which may contain ether linkages between carbon atoms;

m is at least 1; and p provides a moiety weight of 400 to 10,000;

E and E' independently denote a polymerizable unsaturated organic radical represented by formula (VIII):

$$R^{13}-CH=\overset{\overset{R^{12}}{|}}{C}-(CH_2)_w-(X)_x-(Z)_z-(Ar)_y-R^{14}- \quad \text{(VIII)}$$

wherein: $R^{14}$ denotes a divalent alkylene radical having 1 to 10 carbon atoms;

$R^{12}$ denotes H or $CH_3$;

$R^{13}$ denotes H, a ($C_1$-$C_6$) alkyl radical or a —CO—Y—$R^{15}$ group wherein Y is —O—, —S— or —NH— and $R^{15}$ is a alkyl radical having 1 to 12 carbon atoms;

X is —CO— or —OCO—;

Z is —O— or —NH—;

Ar denotes an aromatic radical having 6 to 30 carbon atoms;

w is 0 to 6;

x is 0 or 1;

y is 0 or 1; and z is 0 or 1.

A preferred urethane monomer is represented by formula (IX):

$$\begin{array}{l}H_2C=\overset{CH_3}{\underset{|}{C}}\\ \phantom{H_2C=}COOCH_2CH_2\end{array}\left[\begin{array}{c}\overset{H}{\underset{|}{OCN}}-R^{16}-\overset{H}{\underset{|}{NCOCH_2CH_2OCH_2CH_2OCN}}-R^{16}-\overset{H}{\underset{|}{NCO(CH_2)_m}}\\ \parallel \phantom{OCN} \parallel \phantom{NCOCH_2CH_2OCH_2CH_2OCN} \parallel \phantom{R^{16}} \parallel\\ O \phantom{OCN} O \phantom{NCOCH_2CH_2OCH_2CH_2OCN} O \phantom{R^{16}} O\end{array}\right.$$

$$\left.\begin{array}{c} \left(\begin{array}{c}CH_3-Si-CH_3\\ |\\ O\\ |\\ CH_3-Si-CH_3\\ |\\ (CH_2)_n\end{array}\right)_p\end{array}\right]_a$$

$$\begin{array}{l}H_2C=\overset{CH_3}{\underset{|}{C}}\\ \phantom{H_2C=}COOCH_2CH_2OCN-R^{16}-NCOCH_2CH_2OCH_2CH_2OCN-R^{16}-NCO\\ \phantom{H_2C=COOCH_2CH_2}\parallel\phantom{R^{16}}\parallel\phantom{NCOCH_2CH_2OCH_2CH_2OCN}\parallel\phantom{R^{16}}\parallel\\ \phantom{H_2C=COOCH_2CH_2}O\phantom{R^{16}}O\phantom{NCOCH_2CH_2OCH_2CH_2OCN}O\phantom{R^{16}}O\end{array}$$

wherein:

$R^{16}$ is a diradical of a diisocyanate after removal of the isocyanate group, and is most preferably the diradical of isophorone diisocyanate, and m, p and a are the same as previously defined. Preferably, the sum of m and a is 3 or 4, and more preferably, a is 1 and m is 3 or 4. Preferably, p is at least 30.

The wettable silicone-containing hydrogels of the present invention, when used in contact lens applications, can produce a wide variety of types of hydrogel contact lenses. As is understood in the field, in general, hydrogel contact lenses should have oxygen permeabilities with DK values greater than about $20 \times 10^{-11}$ $cm^3 \times cm/sec \times cm^2 \times mmHg$ (or 20 DK units) and preferably greater than about 60 DK. They should have a Young's modulus of elasticity in the range of about 5 to 400 g/mm$^2$, preferably greater than about 20 g/mm$^2$ as measured by ASTM test method D1938. Their water content should be between about 10 and 80 %, and preferably between 20 and 60%. The contact angle, which is a measurement of the wettability of the lens, should be less than about 80 degrees and should preferably be-less than about 40 degrees.

The preferred range of the combined vinyl-containing and acrylic-containing hydrophilic wetting monomer concentration is from about 5 weight percent of the polymeric hydrogel mix to about 80 weight percent, and more preferably from about 20 weight percent to about 60 weight percent. The weight ratio of vinyl-containing monomer to acrylic-containing monomer is from about 40:1 to about 1:40, and is preferably higher than 1:1.

The present invention further provides articles of manufacture which can be used for biomedical devices, such as, contact lenses, surgical devices, heart valves, vessel substitutes, intrauterine devices, membranes and other films, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, intraocular devices, and especially contact lenses.

It is known that blood, for example, is readily and rapidly damaged when it comes into contact with artificial surfaces. The design of a synthetic surface which is antithrombogenic and nonhemolytic to blood is necessary for prostheses and devices used with blood.

The terms "shaped articles for use in biomedical applications" or "biomedical devices" mean the materials disclosed herein have physicochemical properties rendering them suitable for prolonged contact with living tissue, blood and the mucous membranes.

Although the exact mechanisms are not fully understood at the present time, the wetting agents of the present invention appear to reduce the deposition problems normally associated with, and believed to be caused by, the high hydrophobicity of the hydrophobic silicone-containing monomers.

Further, the wetting agents of the present invention significantly reduce the contact angle of the surface—a clear indication to those skilled in the field that enhanced wetting has occurred. The resulting novel hydrogels comprising the wetting agents of the present invention were unexpectedly hydrolytically stable, within an acceptable range, while collecting only an acceptable level of deposits.

Two preferred classes of silicone-containing monomers contemplated by the present invention are urethane-containing prepolymers, and ethylenically terminated polysiloxane containing monomers as previously described herein, such as, most preferably $\alpha,\omega$ bis(methacryloxyalkyl)polysiloxane.

The resulting polymers and copolymers disclosed herein can be boiled and/or autoclaved in water without being damaged whereby sterilization may be achieved. Thus, an article formed from the disclosed polymers and copolymers may be used, for example, in surgery where an article is needed which is compatible with living tissue or with the mucous membranes.

The monomer mixes employed in this invention, can be readily cured to cast shapes by conventional methods such as UV polymerization, or thermal polymerization, or combinations thereof, as commonly used in polymerizing ethylenically unsaturated compounds. Representative free radical thermal polymerization initiators are organic peroxides, such as acetal peroxide, lauroyl peroxide, decanoyl peroxide, stearoyl peroxide, benzoyl peroxide. tertiarybutyl peroxypivalate, peroxydicarbonate, and the like, employed in a concentration of about 0.01 to 1 percent by weight of the total monomer mixture. Representative UV initiators are those known in the field such as, benzoin methyl ether, benzoin ethyl ether, Darocure 1173, 1164, 2273, 1116, 2959, 3331 (EM Industries) and Igracure 651 and 184 (Ciba-Geigy).

Polymerization of the monomer mix of this invention may be performed in the presence of a diluent. The polymerization product will then be in the form of a gel. If the diluent is nonaqueous, the diluent must be removed from the gel and replaced with water through the use of extraction and hydration protocols well known to those skilled in the art.

It is also possible to perform the polymerization in the absence of diluent to produce a xerogel. These xerogels may then be hydrated to form the hydrogels as is well known in the art.

In addition to the above-mentioned polymerization initiators, the copolymer of the present invention may also include other monomers as will be apparent to one skilled in the art. For example, the monomer mix may include additional hydrophilic monomers, colorants, curing agents, or UV-absorbing and toughening agents such as those known in the contact lens art.

The polymers of this invention can be formed into contact lenses by spincasting processes (such as those disclosed in U.S. Pat. Nos. 3,408,429 and 3,496,254), cast molding processes (such as those disclosed in U.S. Pat. Nos. 4,084,459 and 4,197,266), combinations of methods thereof, or any other known method for making contact lenses. Polymerization may be conducted either in a spinning mold, or a stationary mold corresponding to a desired contact lens shape. The lens may be further subjected to mechanical finishing, as occasion demands. Polymerization may also be conducted in an appropriate mold or vessel to form buttons, plates or rods, which may then be processed (e.g., cut or polished via lathe or laser) to give a contact lens having a desired shape.

The hydrogels the present invention are oxygen transporting, hydrolytically stable, biologically inert, and transparent. The monomers and prepolymers employed in accordance with this invention, are readily polymerized to form three dimensional networks which permit the transport of oxygen and are optically clear, strong and hydrophilic.

The relative softness or hardness of the contact lenses fabricated from the resulting polymer of this invention can be varied by deceasing or increasing the molecular weight of the polysiloxane prepolymer end-capped with the activated unsaturated group or by varying the percent of the comonomer. As the ratio of polysiloxane units to end-cap units increases, the softness of the material increases.

The following examples serve only to further illustrate aspects of the present invention and should not be construed as limiting the invention.

The following abbreviations are defined as follows:

| | |
|---|---|
| NVP | is N-vinyl pyrrolidone |
| DMA | is N,N-dimethyl acrylamide |
| HEMAVc | is methacryloxyethyl vinyl carbonate |
| TRIS | is methacryloxypropyl tris(trimethylsiloxy)silane |
| IDS3H | is a urethane prepolymer derived from isophorone diisocyante, diethylene glycol, polysiloxanediol encapped with 2-hydroxyethyl methacrylate |
| $M_2D_x$ | is an a,x-bis(methacryloxyalkyl)-polysiloxane |
| VDMO | is 2-vinyl-4,4-dimethyl-2-oxazoline-5-one |

EXAMPLES 1–6

Polyurethane-silicone Hydrogels

Six polyurethane hydrogel films containing the following ingredients, were prepared:

a) IDS3H, 30 parts;

b) TRIS, 30 parts;

c) NVP, varied from 0 to 40 parts;

d) DMA, varied from 40 to 0 parts (NVP+DMA=40parts)

e) Methacryloxyethylvinyl carbonate (HEMAVc crosslinker) at 0.3% of NVP amount;

f) n-Hexanol 40 parts;

g) Darocur-1173, (UV initiator), 0.2 part.

These formulations were UV cured, followed by ethanol extraction and boiling water hydration, as is known in the art, to give resultant hydrogel films with the following properties (water content and modulus). FIG. 1 depicts the resultant films of Examples 1–6 with one plotted point for each film respectively.

TABLE 1

| EXAMPLE | 1 | 2 | 3 | 4 | 5 | 6 |
|---|---|---|---|---|---|---|
| NVP/DMA ratio | 40/0 | 38/2 | 35/5 | 30/10 | 20/20 | 0/40 |
| % water | 35 | 46 | 44 | 41 | 41 | 37 |
| Modulus | 430 | 281 | 150 | 80 | 79 | 63 |

The modulus/composition relationship is depicted in FIG. 1.

EXAMPLE 7

Polyurethane Hydrogel

A formulation was prepared containing the same ingredients and same weight ratios as those in Example 4, except that 3 parts of NVP and 1 part of DMA was replaced by 1 part of VDMO. The formulation was cast onto films and processed as done in Examples 1–6. The resulting hydrogel films had the following properties: water content, 40%; modulus 110 g/mm$^2$.

EXAMPLES 8–11

Polyurethane-silicone Hydrogels

Polyurethane formulations of the ingredients as in Examples 1–6 but of different relative parts, as shown in Table 2, were prepared.

a) IDS3H & b) TRIS, 34 parts each;

c) NVP & d) DMA, 32 parts combined;

e) n-Hexanol, f) HEMAVc and g) Darocure-1173, same parts as in Examples 1–6.

Figure 2:
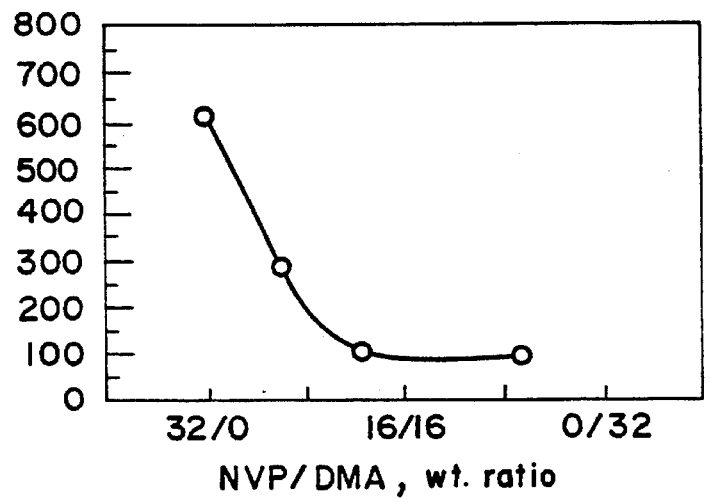

The formulations were cast and processed in the same manner as in Examples 1–6, with the water content and modulus data shown in Table 2. FIG. 2 depicts the resultant films of Examples 8–11, with one plotted point representing each film respectively.

TABLE 2

| EXAMPLE | 8 | 9 | 10 | 11 |
|---|---|---|---|---|
| NVP/DMA ratio | 32/0 | 24/8 | 16/16 | 0/32 |
| water % | 25 | 26 | 31 | 25 |
| Modulus | 610 | 275 | 107 | 87 |

The modulus/composition relationship is further shown in FIG. 2.

EXAMPLES 12–15

$M_2D_x$-based Hydrogel Films

Figure 3:
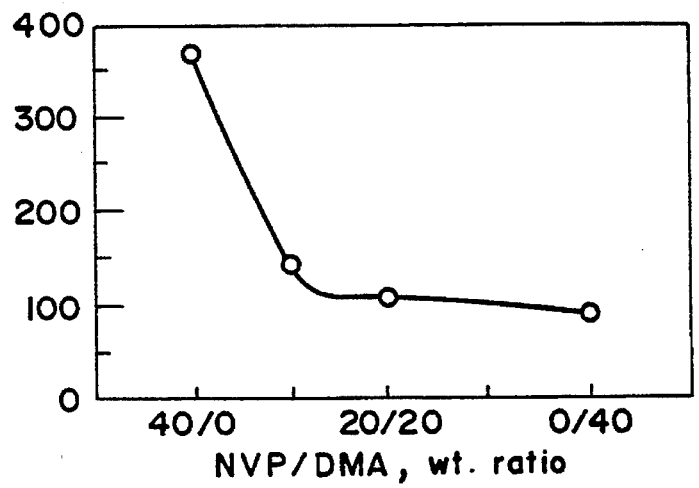
FIG. 3 depicts the effect on modulus of methacrylate-capped polysiloxane films as the composition ratio of NVP to DMA is changed.

The following silicone hydrogel formulations were prepared and cast processed into hydrogel films by the procedure of Examples 8–11. FIG. 3 depicts the resultant films of Examples 8–11, with one plotted point representing each film respectively. The ingredients in the formulation were:

a) $M_2D_x$, 13 parts b) TRIS, 47 parts c) NVP & d) DMA, 40 parts combined e) n-Hexanol, 40 parts f) HEMAVc, 0.3 part of NVP amount g) Darocur, 0.2 part The modulus-composition relationship is depicted in FIG. 3.

EXAMPLE 16

Hydrogel Lens Casting

A monomer mix of the formulation as described in Examples 4, 9, 12 was filtered through a disposable 1.2 micron millipore filter into a clean vial. Under an inert nitrogen atmosphere, 60–90 ul of the mix was injected onto a clean plastic mold half and then covered with a second plastic mold half. The molds were then compressed and cured for 90 minutes in the presence of UV light (4200 microwatts/cm$^2$). The molds were then opened mechanically and put into a beaker containing aqueous ethanol. The lenses were released from the molds within 1 hour, then extracted with ethanol for 48 hours, and boiled in distilled water for 4 hours. The resultant lenses were inspected for cosmetic quality, cytotoxicity and dimensions. Lenses passing inspection were thermally disinfected in phosphate buffered saline prior to on-eye evaluation.

EXAMPLE 17

Clinical Evaluations

The cast-molded polyurethane lenses described in Example 12 were evaluated on six to ten patients. In each test, a poly (HEMA) control lens was worn on one eye and the test lens on the other eye. The lenses were analyzed after a minimum of one hour, and preferably 5 hours or longer for wettability and surface deposition study. The surface wettability rating scale was 0–4 with 0 representing $\frac{2}{3}$ of the anterior surface unwetted by the tear film, and 4 representing complete wetting. The deposition scale was also 0–4 with 0 representing no surface deposits and 4 representing multiple deposits of 0.5 mm diameter or larger. The results for the lenses of the control formulation (according to Example 4) was 3.0 for wetting and 0.4 for deposits after five hours of wear. For lenses comprising 1 part of VDMO (Example 7 formulation), the results showed a wettability rating of 3.3 and a deposit rating of 0.7 after 5 hours or wear.

Many other modifications and variations of the present invention are possible to the skilled practitioner in the field in light of the teachings herein. It is therefore understood that, within the scope of the claims, the present invention can be practiced other than as herein specifically described.

We claim:

1. In a silicone-containing hydrogel composition formed by curing a monomer mixture comprising at least one silicone-containing monomer and a hydrophilic monomer, the improvement of which comprises combining the silicone-containing monomer with N-vinylpyrrolidone and N,N-dimethylacrylamide in the monomer mixture.

2. The hydrogel of claim 1 wherein the weight ratio of N-vinylpyrrolidone to N,N-dimethylacrylamide present in the monomer mixture is from about 1:40 to about 40:1

3. The hydrogel of claim 1 wherein the combined weight percent of N-vinyl pyrrolidone and N,N-dimethyl acrylamide in the monomer mixture is from about 5 to about 80 weight percent.

4. The hydrogel of claim 1 wherein the combined weight percent of N-vinyl pyrrolidone and N,N-dimethyl acrylamide in the monomer mixture is from about 20 to about 60 weight percent of the polymeric hydrogel mixture.

5. The hydrogel of claim 1 wherein the Young's modulus of elasticity of the silicone containing hydrogel is from about 5 g/mm$^2$ to about 400 g/mm$^2$.

6. The hydrogel of claim 1 wherein the silicone-containing monomer is a polyorganosiloxane monomer.

7. The hydrogel of claim 1 wherein the silicone-containing monomer is an α, ω bis(methacryloxyalkyl) dimethacrylate polysiloxane.

8. The hydrogel of claim 1 wherein the silicone-containing monomer is a bulky polysiloxanylalkyl (meth)acrylate monomer.

9. The hydrogel of claim 8 wherein the bulky polysiloxanylalkyl (meth)acrylate monomer is selected from the group consisting of methyloxypropyl tris(trimethylsiloxy) silane, pentamethyldisiloxanylmethylmethacrylate, tris(trimethylsiloxy)methacryloxy propylsilane, phenyltetramethyldisiloxanylethyl acrylate, and methyldi(trimethylsiloxy)methacryloxymethyl silane.

10. The hydrogel of claim 1 wherein the monomer mixture comprises N-vinylpyrrolidone, N,N-dimethylacrylamide and an α, ω bis(methacryloxyalkyl)dimethacrylate polysiloxane.

11. In a contact lens formed from the polymerization product of a monomer mixture comprising at least one silicone-containing monomer and a hydrophilic monomer, the improvement of which comprises combining N-vinylpyrrolidone and N,N-dimethylacrylamide with the silicone-containing monomer in the monomer mixture.

12. The contact lens of claim 11 wherein the weight ratio of N-vinylpyrrolidone to N,N-dimethylacrylamide present is from about 1:40 to about 40:1.

13. The contact lens of claim 11 wherein the combined weight percent of N-vinyl pyrrolidone and N,N-dimethyl acrylamide in the monomer mixture is from about 5 to about 80 weight percent of the polymeric hydrogel mixture.

14. The contact lens of claim 11 wherein the combined weight percent of N-vinyl pyrrolidone and N,N-dimethyl acrylamide in the monomer mixture is from about 20 to about 60 weight percent of the polymeric hydrogel mixture.

15. The contact lens of claim 11 wherein the Young's modulus of elasticity is from about 5 g/mm$^2$ to about 400 g/mm$^2$.

16. The contact lens of claim 11 comprising N-vinylpyrrolidone, N,N-dimethylacrylamide and an α, ω bis-(methacryloxyalkyl)dimethacrylate polysiloxane.

\* \* \* \* \*

UNITED STATES PATENT AND TRADEMARK OFFICE
CERTIFICATE OF CORRECTION

PATENT NO. : 5,486,579
DATED : January 23, 1996
INVENTOR(S) : Yu-Chin Lai and Paul L. Valint, Jr.

It is certified that error appears in the above-indentified patent and that said Letters Patent is hereby corrected as shown below:

In Column 7, line 62, change "benzoyl peroxide. tertiarybutyl" to
-- benzoyl peroxide, tertiarybutyl -- .

In Column 10, line 52, change "5 hours or wear." to -- 5 hours of wear. -- .

In Column 11, line 4, change "weight percent." to
-- weight percent of the polymeric hydrogel mixture. -- .

In Column 11, line 14, change "claim 1" to -- claim 6 -- .

Signed and Sealed this

Fourth Day of June, 1996

Attest:

BRUCE LEHMAN

*Attesting Officer*     *Commissioner of Patents and Trademarks*